US011692954B1

(12) United States Patent
Du et al.

(10) Patent No.: US 11,692,954 B1
(45) Date of Patent: Jul. 4, 2023

(54) TRACE DETECTION METHOD OF HEAVY METALS AND APPLICATION THEREOF

(71) Applicant: Quality standards & Testing Technique of Research Institute, Yunnan Academy of Agricultural Sciences, Kunming (CN)

(72) Inventors: LiJuan Du, Kunming (CN); QiWan Li, Kunming (CN); Tao Lin, Kunming (CN); YanPing Ye, Kunming (CN); MaoQiong Wei, Kunming (CN); YaNan Bi, Kunming (CN)

(73) Assignee: QUALITY STANDARDS & TESTING TECHNIQUE OF RESEARCH INSTITUTE, YUNNAN ACADEMY OF AGRICULTURAL SCIENCES, Kunming (CN)

( * ) Notice: Subject to any disclaimer, the term of this patent is extended or adjusted under 35 U.S.C. 154(b) by 0 days.

(21) Appl. No.: 18/079,405

(22) Filed: Dec. 12, 2022

(30) Foreign Application Priority Data

Mar. 16, 2022 (CN) .......................... 202210258214.3

(51) Int. Cl.
*G01N 21/64* (2006.01)
*G01N 23/223* (2006.01)
*G01N 33/14* (2006.01)

(52) U.S. Cl.
CPC ........... *G01N 23/223* (2013.01); *G01N 33/14* (2013.01); *G01N 2223/076* (2013.01); *G01N 2223/60* (2013.01)

(58) Field of Classification Search
CPC .......... G01N 33/5008; G01N 33/6842; G01N 2035/00326; G01N 2021/7786; G01N 2035/00465; G01N 2223/076; G01N 33/02; G01N 33/20; G01N 35/00584; G01N 21/643; G01N 21/6447; C12N 2523/00; C12N 1/20
See application file for complete search history.

(56) References Cited

U.S. PATENT DOCUMENTS

2022/0178824 A1* 6/2022 Berekaa ................. C12N 1/205

* cited by examiner

*Primary Examiner* — Don K Wong
(74) *Attorney, Agent, or Firm* — WPAT, PC

(57) ABSTRACT

The invention belongs to the technical field of trace detection, and discloses a heavy metal trace detection method and application thereof. The detection method; comprising the following steps: preparing a quality sample; mixing the quality sample with the sample to be tested according to a specific proportion; using X-ray fluorescence spectrometer to detect trace heavy metals; and using standard curve to realize quantitative analysis of heavy metals. For the purpose of detecting heavy metal elements in tea, the application of this invention can shorten the detection time, avoid the use of a large amount of acid liquor, improve the environmental protection performance, and lower the detection cost, moreover, the obtained standard curve by this invention has high correlation and accurate detection results.

2 Claims, 1 Drawing Sheet

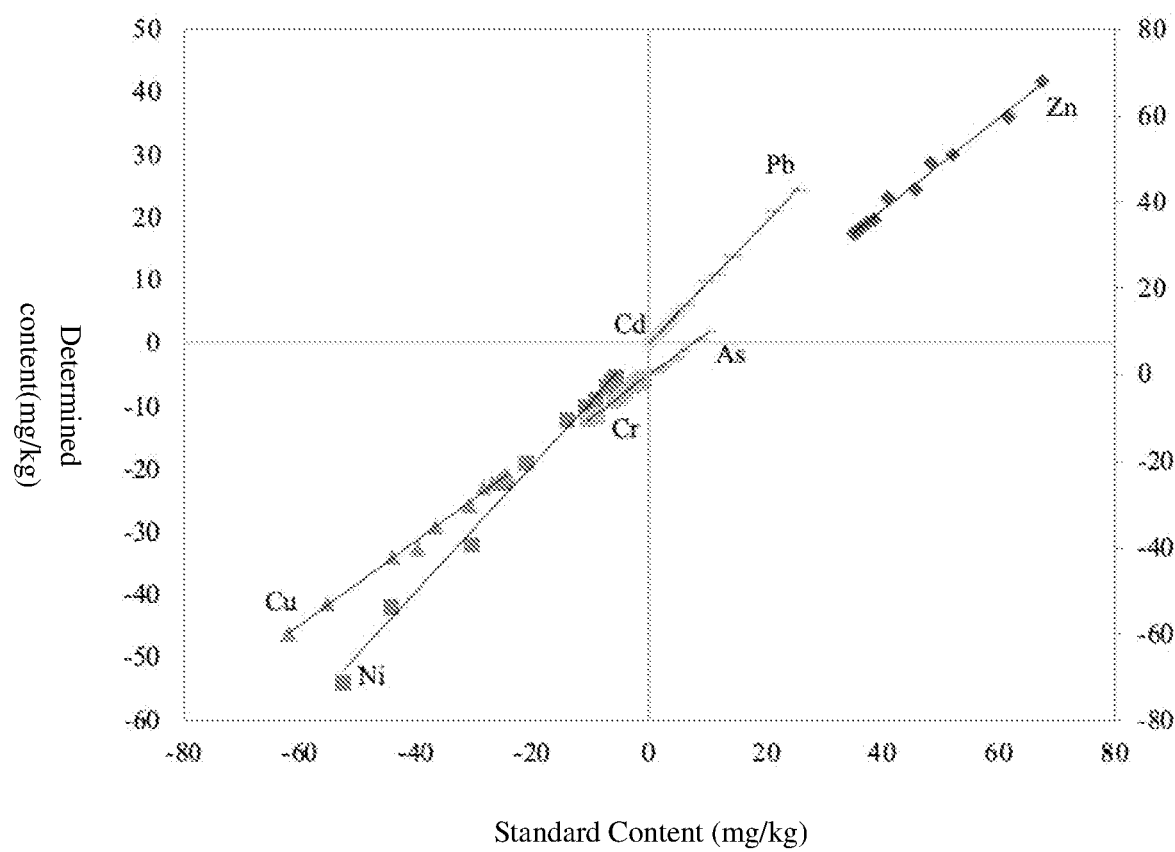

TRACE DETECTION METHOD OF HEAVY METALS AND APPLICATION THEREOF

TECHNICAL FIELD

This invention relates to the technical field of trace detection, particularly related to trace detection method of heavy metals and application thereof.

BACKGROUND

After human consumes foods containing heavy metals, the heavy metals would accumulate in human body, then it would be extremely difficult to degrade and remove the enriched heavy metals out of human body, therefore, even a very small amount of heavy metals can still be harmful to human body due to the enrichment. Heavy metals can interact strongly with protein, enzymes, etc. inside human body, making them lose their activity, or they may accumulate in human organs, causing chronic poisoning.

However, the content of heavy metals in tea is very low, it is difficult to directly detect them by instruments, therefore, the common solution is to apply pretreatment of acid digestion, but, the conventional acid digestion process takes a lot of time, and the accuracy of its testing results is easily affected because of the errors exist in the process of pretreatment of acid digestion.

The prior art uses microwave digestion/wet digestion to pretreat samples, and uses atomic absorption spectrometry/atomic fluorescence spectrometry/inductively coupled plasma mass spectrometry to determine the content of heavy metals in tea samples. However, the following problems still exist in the prior art:

1. a big amount of acid is used during pretreatment, and massive acid mists generated during digestion pollute the environment to a certain extent, and have adverse effects on the health of lab testing personnel;

2. pretreatment of acid digestion is the process of oxidizing organic substances in samples with high-grade nitric acid, perchloric acid, etc. to produce inorganic ions, the process takes longer time, and demands higher economic and time cost.

Therefore, it is urgent to provide a trace detection method of heavy metals and application thereof, which can shorten the detection time of heavy metals in tea, avoid the use massive acid, and reduce the detection cost.

SUMMARY

In view of this, the invention provides trace detection method of heavy metals and application thereof, which improves the detection efficiency of heavy metals in tea, reduces the detection cost and meets the requirements of environmental protection.

Trace detection method of heavy metals, comprising the following steps:

1) preparing a quality sample;

2) mixing the quality sample with the sample to be tested according to a specific proportion;

3) using X-ray fluorescence spectrometer to detect trace heavy metals.

Preferably, the preparation steps of the quality sample in step 1) are as follows: as shown in Table 1, each single standard solution is added to the tea quality sample of GBW 08505, after the addition, the quality sample is freeze-dried, ground at −4° C., evenly mixed and bottled for later use. According to the standard requirements of "CNAS-G017-2018 General Principles and Statistical Methods of Standard Reference Materials/Standard Samples", carrying out the homogeneity test, stability test, uncertainty evaluation, data evaluation, etc. on the quality samples, setting value on the new quality samples for the use laboratory internal control.

TABLE 1

| | Quality of spiked standard of each element | | | | | | |
|---|---|---|---|---|---|---|---|
| | As | Pb | Cd | Cr | Cu | Zn | Ni |
| Single standard solution (mg/L) | 1000 | 1000 | 1000 | 1000 | 1000 | 1000 | 1000 |
| Content of quality sample after spiked standard solution (mg/kg) | 20 | 50 | 10 | 20 | 100 | 100 | 100 |
| Spike mass of single standard solution (mg) | 0.1894 | 0.4894 | 0.09968 | 0.192 | 0.838 | 0.613 | 0.9239 |

Preferably, the heavy metals include As, Pb, Cd, Cr, Cu, Zn and Ni.

Preferably, in step 2, when the heavy metal element detected is As, the mass ratio of quality control sample to sample to be detected is 20:0.27;

when the heavy metal element detected is Pb, the mass ratio of the quality control sample to the sample to be detected is 20:0.27;

when the detected heavy metal element is Cd, the mass ratio of the quality control sample to the sample to be detected is 50:1.6;

when the detected heavy metal element is Cr, the mass ratio of the quality control sample to the sample to be detected is 10:0.076;

when the heavy metal element detected is Cu, the mass ratio of the quality control sample to the sample to be detected is 100:24;

when the heavy metal element detected is Zn, the mass ratio of the quality control sample to the sample to be detected is 100:35;

when the heavy metal element detected is Ni, the mass ratio of quality control sample to sample to be detected is 100:5.4.

Preferably, in step 3, the test conditions of X-ray fluorescence spectrometer are described as follows: current range of X-ray tube is 0~0.2 mA, voltage range is 0~70 KV, test time range is 0~10 min, collimator is φ5 mm, the optical filter system, containing 4 optical filters, wherein, the optical filter is optimized by heavy metal detection and can be automatically switched, the target excitation, containing a Micro X-ray window.

The other purpose of this invention is to provide the application of trace detection method of heavy metals.

Comparing with the prior art, this invention has the following beneficial effects:

The invention applies the combination of the standard addition method with XRF (X-ray fluorescence spectrometer) to measure the content of heavy metals in tea, which does not need acid digestion, and the test method is simple and efficient; before using XRF for determination, the quality sample is quantitatively added to the sample to be detected, which eliminates the loss and pollution of acid solution, achieves the effect of enriching the elements to be detected, and improves the accuracy of XRF for the detection of heavy metals.

The principle of X-ray fluorescence spectrometer (XRF) for determining the content of elements is: different elements have characteristic X-ray spectra with different wavelengths, and the fluorescence intensity of each spectral line is linearly related to the concentration of elements, therefore, qualitative and quantitative analysis of the elements to be tested can be realized by measuring the wavelength and intensity of the characteristic X-ray lines of elements. Portable XRF can realize in-situ detection of heavy metals, it has advantages of being non-destructive to the sample, and achieving simultaneous determination of multiple elements of the sample, moreover, the detection process takes shorter time, and is easy to operate with lower cost and timely data provision.

BRIEF DESCRIPTION OF DRAWINGS

FIG. 1 illustrates the standard curve of heavy metals in tea.

DETAILED DESCRIPTION OF EMBODIMENTS

Trace detection method of heavy metals, comprising the following steps:
1) preparing a quality sample;
2) mixing the quality sample with the sample to be tested according to a specific proportion;
3) using X-ray fluorescence spectrometer to detect trace heavy metals.

According to this invention, the preparation steps of the quality sample in step 1) are as follows: as shown in Table 1, each single standard solution is added to the tea quality sample of GBW 08505, after the addition, the quality sample is freeze-dried, and ground at −4° C., evenly mixed and bottled for later use. According to the standard requirements of "CNAS-G017-2018 General Principles and Statistical Methods of Standard Reference Materials/Standard Samples", carrying out the homogeneity test, stability test, uncertainty evaluation, data evaluation, etc. on the quality samples, setting value on the new quality samples for the use laboratory internal control.

According to this invention, the heavy metals include As, Pb, Cd, Cr, Cu, Zn and Ni.

According to this invention, in step 2,
when the heavy metal element detected is As, the mass ratio of quality control sample to sample to be detected is 20:0.27;
when the heavy metal element detected is Pb, the mass ratio of the quality control sample to the sample to be detected is 20:0.27;
when the detected heavy metal element is Cd, the mass ratio of the quality control sample to the sample to be detected is 50:1.6;
when the detected heavy metal element is Cr, the mass ratio of the quality control sample to the sample to be detected is 10:0.076;
when the heavy metal element detected is Cu, the mass ratio of the quality control sample to the sample to be detected is 100:24;
when the heavy metal element detected is Zn, the mass ratio of the quality control sample to the sample to be detected is 100:35;
when the heavy metal element detected is Ni, the mass ratio of quality control sample to sample to be detected is 100:5.4.

According to this invention, in step 3, the test conditions of X-ray fluorescence spectrometer are described as follows: current range of X-ray tube is 0~0.2 mA, voltage range is 0~70 KV, test time range is 0~10 min, collimator is φ5 mm, the optical filter system, containing 4 optical filters, wherein, the optical filter is optimized by heavy metal detection and can be automatically switched, the target excitation, containing a Micro X-ray window.

Drawing of Standard Curve:

The standard curve is based on the standard content of the sample to be tested and the content measured by the instrument, wherein, the two contents shows a linear relationship with the different spike mass. The higher the linear correlation, the more accurate the determination.

As shown in Table 2, adding the quality sample to the sample to be tested, fully mixing, then measuring the content of each element with X-ray fluorescence instrument, setting the determined value as the ordinate, setting the theoretical standard content, which is calculated after adding the spiking solution, as the abscissa, drawing the standard curve, fitting the linear equation, and calculating the spiked recovery (see FIG. 1, Table 3 and Table 4 for details).

TABLE 2

Quality of spiked quality control samples (unit: g)

| No. | As | Pb | Cd | Cr | Cu | Zn | Ni |
|---|---|---|---|---|---|---|---|
| 1 | 0.01 | 0.01 | 0.01 | 0.01 | 0.01 | 0.01 | 0.01 |
| 2 | 0.02 | 0.02 | 0.02 | 0.02 | 0.02 | 0.02 | 0.02 |
| 3 | 0.05 | 0.05 | 0.05 | 0.05 | 0.05 | 0.05 | 0.05 |

TABLE 1

Quality of addition standard of each element

| | As | Pb | Cd | Cr | Cu | Zn | Ni |
|---|---|---|---|---|---|---|---|
| Single standard solution (mg/L) | 1000 | 1000 | 1,000 | 1000 | 1000 | 1000 | 1000 |
| Content of quality sample after spiked standard solution (mg/kg) | 20 | 50 | 10 | 20 | 100 | 100 | 100 |
| Spike mass of single standard solution (mg) | 0.1894 | 0.4894 | 0.09968 | 0.192 | 0.838 | 0.613 | 0.9239 |

TABLE 2-continued

Quality of spiked quality control samples (unit: g)

| No. | As | Pb | Cd | Cr | Cu | Zn | Ni |
|---|---|---|---|---|---|---|---|
| 4 | 0.1 | 0.1 | 0.1 | 0.1 | 0.1 | 0.1 | 0.1 |
| 5 | 0.2 | 0.2 | 0.2 | 0.2 | 0.2 | 0.2 | 0.2 |
| 6 | 0.3 | 0.3 | 0.3 | 0.3 | 0.3 | 0.3 | 0.3 |
| 7 | 0.5 | 0.5 | 0.5 | 0.5 | 0.5 | 0.5 | 0.5 |
| 8 | 1 | 1 | 1 | 1 | 1 | 1 | 1 |
| 9 | 1.3 | 1.3 | 1.3 | 1.3 | 1.3 | 1.3 | 1.3 |
| 10 | 1.8 | 1.8 | 1.8 | 1.8 | 1.8 | 1.8 | 1.8 |
| 11 | 3.5 | 3.5 | 3.5 | 3.5 | 3.5 | 3.5 | 3.5 |
| 12 | 5 | 5 | 5 | 5 | 5 | 5 | 5 |

TABLE 3

Standard curve and correlation coefficient of heavy metals in tea

| No. | Standard curve | correlation coefficient R2 |
|---|---|---|
| As | y = 0.9817x − 0.0697 | 0.9992 |
| Pb | y = 0.9596x + 0.0333 | 0.9984 |
| Cd | y = 1.0133x − 0.0214 | 0.9995 |
| Cr | y = 1.0055x − 0.0346 | 0.9943 |
| Cu | y = 0.9777x − 0.6403 | 0.9965 |
| Zn | y = 1.0666x − 4.5605 | 0.9920 |
| Ni | y = 1.0051x − 0.8094 | 0.9924 |

TABLE 4

Spike recovery value of heavy metals
(As, Pb, Cd, Cr, Cu, Zn, Ni) in tea (unit: %)

| No | As | Pb | Cd | Cr | Cu | Zn | Ni |
|---|---|---|---|---|---|---|---|
| 1 | 104.18 | 85.82 | 114.81 | 92.89 | 97.30 | 93.94 | 96.62 |
| 2 | 101.69 | 90.64 | 106.46 | 110.44 | 96.70 | 93.59 | 93.48 |
| 3 | 95.76 | 91.33 | 101.00 | 108.21 | 94.94 | 92.58 | 96.27 |
| 4 | 93.37 | 92.55 | 104.70 | 102.00 | 94.15 | 93.73 | 96.49 |
| 5 | 87.28 | 96.29 | 94.89 | 94.33 | 92.86 | 93.33 | 98.47 |
| 6 | 88.98 | 94.75 | 96.00 | 94.50 | 91.87 | 93.07 | 92.98 |
| 7 | 91.93 | 102.00 | 98.94 | 92.29 | 97.06 | 100.22 | 85.71 |
| 8 | 93.58 | 103.45 | 95.55 | 97.07 | 95.45 | 93.82 | 89.76 |
| 9 | 92.37 | 93.98 | 98.88 | 102.53 | 100.80 | 101.21 | 88.28 |
| 10 | 99.02 | 96.80 | 98.41 | 96.98 | 95.20 | 97.69 | 105.12 |
| 11 | 96.64 | 97.54 | 101.70 | 107.10 | 95.85 | 97.14 | 94.69 |
| 12 | 98.56 | 94.30 | 101.69 | 96.56 | 96.77 | 100.74 | 102.47 |

This invention also provides the application of of trace detection method of heavy metals.

The technical solutions in the embodiments of the present invention will be clearly and completely described below. Obviously, the described embodiments are only part of the embodiments of the present invention, but not all of them. Based on the embodiment of the present invention, all other embodiments obtained by ordinary technicians in the field without creative labor are within the scope of the present invention.

EMBODIMENT 1

30 tea samples were randomly determined by ICP-MS and X-ray fluorescence instrument, and the relative phase differences between the two independent determination results were calculated, and the results respectively were As 0.34-13.35%, Pb 0.70-11.34%, Cd 0.73-14.97%, Cr 0.61-9.66%, Cu 0.15-7.05%, Zn 0.38-13.20%, Ni 0.28-9.52%, average<20%, meeting the requirements of GB 5009.268 for precision. (The relative phase difference of two independent determination results, when the content>1 mg/kg, the relative phase difference 10%; When the relative phase difference of content≤1 mg/kg and >0.1 mg/kg, the relative phase difference is ≤15%; When the content is ≤0.1 mg/kg, the relative phase difference is ≤20%).

TABLE 5.1

Determination content (mg/kg) and relative phase difference (%) of tea samples

| | As | | | Pb | | | Cd | | | Cr | | |
|---|---|---|---|---|---|---|---|---|---|---|---|---|
| No | ICPMS | XRF | RSD % | ICPMS | XRF | RSD % | ICPMS | XRF | RSD % | ICPMS | XRF | RSD % |
| 1 | 0.1901 | 0.2032 | −6.66 | 0.7687 | 0.8456 | −9.53 | 0.0527 | 0.0554 | −4.95 | 2.3843 | 2.3223 | 2.64 |
| 2 | 0.0934 | 0.1009 | −7.70 | 0.4748 | 0.5210 | −9.28 | 0.1779 | 0.1878 | −5.40 | 0.7438 | 0.7220 | 2.97 |
| 3 | 0.0877 | 0.1000 | −13.15 | 0.5320 | 0.5543 | −4.10 | 0.1613 | 0.1778 | −9.71 | 0.7346 | 0.7301 | 0.61 |
| 4 | 0.0676 | 0.0760 | −11.76 | 0.0675 | 0.0700 | −3.68 | 0.0222 | 0.0253 | −12.99 | 0.9603 | 1.0012 | −4.17 |
| 5 | 0.0962 | 0.1103 | −13.70 | 0.0698 | 0.0770 | −9.86 | 0.0231 | 0.0268 | −14.97 | 1.2691 | 1.2234 | 3.67 |
| 6 | 0.0772 | 0.0801 | −3.74 | 0.0888 | 0.0987 | −10.55 | 0.0217 | 0.0245 | −11.97 | 1.2512 | 1.2121 | 3.17 |
| 7 | 0.0522 | 0.0560 | −7.05 | 0.5416 | 0.5454 | −0.70 | 0.0344 | 0.0339 | 1.52 | 0.9402 | 1.0111 | −7.27 |
| 8 | 0.0700 | 0.0711 | −1.54 | 0.0406 | 0.0450 | −10.19 | 0.0221 | 0.0237 | −6.97 | 0.9149 | 0.9238 | −0.97 |
| 9 | 0.0335 | 0.0355 | −5.82 | 0.0199 | 0.0222 | −11.07 | 0.0488 | 0.0500 | −2.48 | 0.7583 | 0.8019 | −5.58 |
| 10 | 0.0946 | 0.1023 | −7.78 | 0.1084 | 0.1145 | −5.52 | 0.0286 | 0.0301 | −5.17 | 1.2650 | 1.2323 | 2.62 |
| 11 | 0.1035 | 0.1131 | −8.87 | 0.1613 | 0.1789 | −10.33 | 0.0300 | 0.0321 | −6.74 | 1.3297 | 1.2444 | 6.63 |
| 12 | 0.1172 | 0.1180 | −0.72 | 0.1413 | 0.1567 | −10.34 | 0.0320 | 0.0311 | 2.98 | 1.0087 | 1.1111 | −9.66 |
| 13 | 0.1180 | 0.1298 | −9.50 | 0.2040 | 0.1976 | 3.17 | 0.0309 | 0.0311 | −0.73 | 1.3035 | 1.2345 | 5.44 |
| 14 | 0.1087 | 0.1212 | −10.87 | 0.2599 | 0.2500 | 3.87 | 0.0322 | 0.0345 | −6.96 | 1.3393 | 1.2988 | 3.07 |
| 15 | 0.1245 | 0.1278 | −2.63 | 0.1267 | 0.1345 | −6.00 | 0.0307 | 0.0298 | 3.10 | 1.1802 | 1.2020 | −1.83 |
| 16 | 0.1583 | 0.1781 | −11.76 | 0.1433 | 0.1345 | 6.35 | 0.0297 | 0.0321 | −7.64 | 1.1273 | 1.2023 | −6.44 |
| 17 | 0.0700 | 0.0789 | −11.88 | 0.0500 | 0.0560 | −11.34 | 0.0176 | 0.0200 | −12.77 | 1.1184 | 1.1987 | −6.93 |
| 18 | 0.1066 | 0.1100 | −3.15 | 0.0165 | 0.0180 | −8.41 | 0.0348 | 0.0333 | 4.35 | 1.0053 | 1.0924 | −8.30 |
| 19 | 0.1954 | 0.2000 | −2.32 | 0.6696 | 0.6634 | 0.93 | 0.1262 | 0.1187 | 6.09 | 1.3884 | 1.2901 | 7.34 |
| 20 | 0.2105 | 0.2000 | 5.11 | 0.1748 | 0.1699 | 2.85 | 0.0972 | 0.0893 | 8.43 | 1.4202 | 1.2998 | 8.86 |
| 21 | 0.2774 | 0.2765 | 0.34 | 0.3066 | 0.2900 | 5.58 | 0.0399 | 0.0387 | 3.03 | 1.2716 | 1.2998 | −2.19 |
| 22 | 0.2618 | 0.2521 | 3.79 | 0.3266 | 0.3000 | 8.48 | 0.0386 | 0.0376 | 2.60 | 1.3766 | 1.2898 | 6.51 |
| 23 | 0.0791 | 0.0800 | −1.11 | 0.0908 | 0.1001 | −9.78 | 0.0412 | 0.0378 | 8.62 | 1.0621 | 1.1213 | −5.42 |
| 24 | 0.0768 | 0.0679 | 12.33 | 0.1300 | 0.1200 | 8.03 | 0.0392 | 0.0411 | −4.81 | 1.0221 | 1.1010 | −7.43 |
| 25 | 0.0795 | 0.0876 | −9.64 | 0.0465 | 0.0502 | −7.75 | 0.0248 | 0.0265 | −6.81 | 1.4714 | 1.4747 | −0.22 |

TABLE 5.1-continued

Determination content (mg/kg) and relative phase difference (%) of tea samples

| | As | | | Pb | | | Cd | | | Cr | | |
|---|---|---|---|---|---|---|---|---|---|---|---|---|
| No | ICPMS | XRF | RSD % | ICPMS | XRF | RSD % | ICPMS | XRF | RSD % | ICPMS | XRF | RSD % |
| 26 | 0.1243 | 0.1421 | −13.35 | 0.0755 | 0.0801 | −5.91 | 0.0279 | 0.0300 | −7.42 | 1.3612 | 1.4721 | −7.83 |
| 27 | 0.1196 | 0.1234 | −3.10 | 0.1302 | 0.1221 | 6.43 | 0.0287 | 0.0300 | −4.58 | 1.2247 | 1.3434 | −9.24 |
| 28 | 0.1202 | 0.1234 | −2.65 | 0.0820 | 0.0890 | −8.18 | 0.0269 | 0.0289 | −7.00 | 1.0938 | 1.1829 | −7.83 |
| 29 | 0.1110 | 0.1098 | 1.05 | 0.1474 | 0.1348 | 8.93 | 0.0251 | 0.0277 | −9.71 | 0.9152 | 1.0000 | −8.85 |
| 30 | 0.1322 | 0.1298 | 1.81 | 0.1321 | 0.1348 | −2.00 | 0.0458 | 0.0444 | 3.11 | 1.1379 | 1.1111 | 2.38 |

TABLE 5.2

Determination content (mg/kg) and relative phase difference (%) of tea samples

| NO | Cu | | | Zn | | | Ni | | |
|---|---|---|---|---|---|---|---|---|---|
| 1 | ICPMS | XRF | RSD % | ICPMS | XRF | RSD % | ICPMS | XRF | RSD % |
| 2 | 99.85 | 100.00 | −0.15 | 0.9444 | 0.9121 | 3.48 | 25.58 | 23.45 | 8.70 |
| 3 | 56.98 | 57.11 | −0.23 | 0.1416 | 0.1421 | −0.38 | 39.78 | 38.77 | 2.57 |
| 4 | 58.15 | 62.23 | −6.78 | 0.2587 | 0.2433 | 6.15 | 41.01 | 39.01 | 5.00 |
| 5 | 61.31 | 62.33 | −1.65 | 0.3930 | 0.4123 | −4.79 | 17.91 | 17.23 | 3.87 |
| 6 | 64.87 | 60.11 | 7.61 | 0.4438 | 0.4189 | 5.77 | 22.34 | 20.92 | 6.55 |
| 7 | 68.53 | 70.23 | −2.46 | 0.5576 | 0.5328 | 4.55 | 23.05 | 22.22 | 3.66 |
| 8 | 54.89 | 58.90 | −7.05 | 0.1481 | 0.1298 | 13.20 | 25.41 | 23.44 | 8.06 |
| 9 | 61.49 | 65.34 | −6.07 | 0.0776 | 0.0809 | −4.11 | 25.31 | 23.01 | 9.52 |
| 10 | 71.64 | 68.99 | 3.77 | 0.2593 | 0.2345 | 10.06 | 32.42 | 30.98 | 4.53 |
| 11 | 72.15 | 70.10 | 2.88 | 0.6226 | 0.5789 | 7.27 | 21.17 | 23.01 | −8.34 |
| 12 | 76.77 | 73.21 | 4.75 | 0.6281 | 0.5982 | 4.88 | 22.12 | 23.89 | −7.67 |
| 13 | 69.83 | 71.34 | −2.13 | 0.3347 | 0.3143 | 6.28 | 26.44 | 24.88 | 6.08 |
| 14 | 73.32 | 71.98 | 1.84 | 0.9550 | 1.0010 | −4.70 | 24.17 | 24.87 | −2.86 |
| 15 | 71.70 | 73.45 | −2.42 | 0.5109 | 0.5347 | −4.55 | 25.15 | 25.55 | −1.59 |
| 16 | 70.35 | 73.21 | −3.98 | 0.4467 | 0.5001 | −11.28 | 29.33 | 30.99 | −5.49 |
| 17 | 70.22 | 73.20 | −4.15 | 0.8682 | 0.8989 | −3.47 | 28.65 | 30.31 | −5.63 |
| 18 | 59.70 | 60.54 | −1.40 | 0.3976 | 0.3876 | 2.54 | 20.94 | 23.03 | −9.51 |
| 19 | 58.77 | 61.10 | −3.90 | 0.7239 | 0.7014 | 3.15 | 25.99 | 26.79 | −3.02 |
| 20 | 73.01 | 70.22 | 3.90 | 0.7980 | 0.8123 | −1.78 | 38.30 | 40.34 | −5.18 |
| 21 | 73.46 | 74.32 | −1.17 | 0.9794 | 0.9432 | 3.77 | 38.77 | 40.98 | −5.54 |
| 22 | 72.86 | 75.27 | −3.25 | 2.1031 | 1.9879 | 5.63 | 26.26 | 26.33 | −0.28 |
| 23 | 76.01 | 75.99 | 0.02 | 1.9324 | 1.9989 | −3.38 | 26.49 | 25.13 | 5.27 |
| 24 | 62.77 | 65.44 | −4.16 | 0.6838 | 0.7089 | −3.60 | 17.16 | 16.77 | 2.32 |
| 25 | 63.35 | 65.01 | −2.58 | 1.0923 | 0.9898 | 9.84 | 17.15 | 17.98 | −4.70 |
| 26 | 95.04 | 98.10 | −3.17 | 0.8633 | 0.9001 | −4.17 | 18.27 | 19.99 | −8.97 |
| 27 | 85.83 | 90.13 | −4.88 | 0.4891 | 0.4678 | 4.45 | 24.86 | 23.23 | 6.78 |
| 28 | 81.70 | 83.33 | −1.97 | 0.8274 | 0.8023 | 3.08 | 23.94 | 21.83 | 9.21 |
| 29 | 70.19 | 72.43 | −3.14 | 0.3092 | 0.3210 | −3.74 | 17.93 | 19.15 | −6.56 |
| 30 | 65.30 | 68.01 | −4.06 | 0.8801 | 0.9032 | −2.59 | 17.48 | 18.43 | −5.27 |

In this specification, each embodiment is described in a progressive way, and the differences between each embodiment and other embodiments are highlighted, so the same and similar parts of each embodiment can be referred to each other. The above description of the disclosed embodiments enables those skilled in the art to make or use the invention. Many modifications to these embodiments will be obvious to those skilled in the art, and the general principles defined herein can be implemented in other embodiments without departing from the spirit or scope of the present invention. Therefore, the present invention will not be limited to the embodiments shown herein, but will be accorded the widest scope consistent with the principles and novel features disclosed herein.

What is claimed is:
1. A trace detection method of heavy metals, comprising steps as follows:
1) Preparing a quality control sample;
2) Mixing the quality control sample with a sample to be tested;
3) Using X-ray fluorescence spectrometer for detection of trace heavy metals;
wherein the heavy metals include As, Pb, Cd, Cr, Cu, Zn and Ni;
wherein in step 2,
when a heavy metal element detected is As, a mass ratio of the quality control sample to the sample to be detected is 20:0.27, a standard curve is y=0.9817x−0.0697, and a correlation coefficient is 0.9992;
when the heavy metal element detected is Pb, the mass ratio of the quality control sample to the sample to be detected is 20:0.27, a standard curve is y=0.9596x+0.0333, and a correlation coefficient is 0.9984;
when the detected heavy metal element is Cd, the mass ratio of the quality control sample to the sample to be detected is 50:1.6, a standard curve is y=1.0133x−0.0214, and a correlation coefficient is 0.9995;
when the detected heavy metal element is Cr, the mass ratio of the quality control sample to the sample to be detected is 10:0.076, a standard curve is y=1.0055x−0.0346, and a correlation coefficient is 0.9943;

when the heavy metal element detected is Cu, the mass ratio of the quality control sample to the sample to be detected is 100:24, a standard curve is y=0.9777x−0.6403, and a correlation coefficient is 0.9965;

when the heavy metal element detected is Zn, the mass ratio of the quality control sample to the sample to be detected is 100:35, a standard curve is y=1.0666x−4.5605, and a correlation coefficient is 0.9920;

when the heavy metal element detected is Ni, the mass ratio of quality control sample to sample to be detected is 100:5.4, a standard curve is y=1.0051x−0.8094, and a correlation coefficient is 0.9924.

2. The trace detection method of heavy metals as claimed in claim 1, wherein in step 3, test conditions of the X-ray fluorescence spectrometer are described as follows: current range of X-ray tube is 0~0.2 mA, voltage range is 0~70 KV, test time range is 0~10 min, collimator is φ5 mm, an optical filter system, containing 4 optical filters, wherein, the optical filter is optimized by heavy metal detection and is automatically switched, target excitation, containing a Micro X-ray window.

\* \* \* \* \*